United States Patent [19]
Soltesz

[11] Patent Number: 5,836,925
[45] Date of Patent: Nov. 17, 1998

[54] CATHETER WITH VARIABLE FLEXIBILITY PROPERTIES AND METHOD OF MANUFACTURE

[76] Inventor: Peter P. Soltesz, 4972 Miramar Ave., San Jose, Calif. 95129

[21] Appl. No.: 824,630

[22] Filed: Mar. 27, 1997

Related U.S. Application Data

[60] Provisional application No. 60/014,552 Apr. 3, 1996.

[51] Int. Cl.$^6$ .................................................. A61M 25/00
[52] U.S. Cl. ........................... 604/280; 604/282; 604/264
[58] Field of Search ..................................... 604/280, 282, 604/264, 281, 283, 265, 266, 270

[56] References Cited

U.S. PATENT DOCUMENTS

| | | | |
|---|---|---|---|
| 4,248,234 | 2/1981 | Assenza et al. | 128/348 |
| 4,606,928 | 8/1986 | Dunford et al. | 427/32 |
| 4,899,787 | 2/1990 | Ouchi et al. | 138/131 |
| 5,037,404 | 8/1991 | Gold et al. | 604/282 |
| 5,176,660 | 1/1993 | Truckai | 604/282 |
| 5,198,281 | 3/1993 | Muzzy et al. | 428/102 |
| 5,226,899 | 7/1993 | Lee et al. | 604/282 |
| 5,254,107 | 10/1993 | Soltesz | 604/282 |
| 5,279,863 | 1/1994 | Escallon | 427/477 |
| 5,308,342 | 5/1994 | Sepetka et al. | 604/282 |
| 5,342,386 | 8/1994 | Trotta | 606/194 |
| 5,445,624 | 8/1995 | Jimenez | 604/280 |
| 5,456,674 | 10/1995 | Bos et al. | 604/280 |
| 5,545,151 | 8/1996 | O'Conner et al. | 604/264 X |
| 5,569,218 | 10/1996 | Berg | 604/264 X |
| 5,599,325 | 2/1997 | Ju et al. | 604/264 X |
| 5,601,538 | 2/1997 | Deem | 604/264 X |
| 5,658,263 | 8/1997 | Dang et al. | 604/264 X |

OTHER PUBLICATIONS

"Electrostatic Wire Coating"—Electrostatic Technology, Inc.
"Teflon Industrial Coatings"—Du Pont Company.
"Electrostatic Spray Gun Selection Guide"—TW Ransburg.
"Fluidized Bed Coating Powder"—Huls.
"Instructions for Powder Coating with Halar"—Whitford Co.
"Electrostatic Powder Spray"—Applied Plastics, Inc.
"Advanced Powder Coatings"—APC, Inc. Div. of Intec.
"Selcting DUPONT Teflon Coatings"—DuPont.

Primary Examiner—Wynn Wood Coggins
Assistant Examiner—N. Kent Gring

[57] ABSTRACT

A catheter having various flexibility properties along the longitudinal extent thereof comprises contiguous tubular segments formed from polymeric materials having various physical properties. To manufacture the catheter, a grounded wire is conveyed through adjacent coating chambers separated by movable walls, each chamber containing an aerated powder of charged polymer particles having a flexibility property. The charged polymer particles are simultaneously deposited on the grounded wire, and then heated and cooled to form a polymeric tube. Each chamber has its own dry air and high voltage power supplies to control the wall thickness of each segment individually. The lengths of the segments are selected by adjusting the walls of the coating chambers, and also by adjusting the sizes of apertures in the walls.

21 Claims, 5 Drawing Sheets

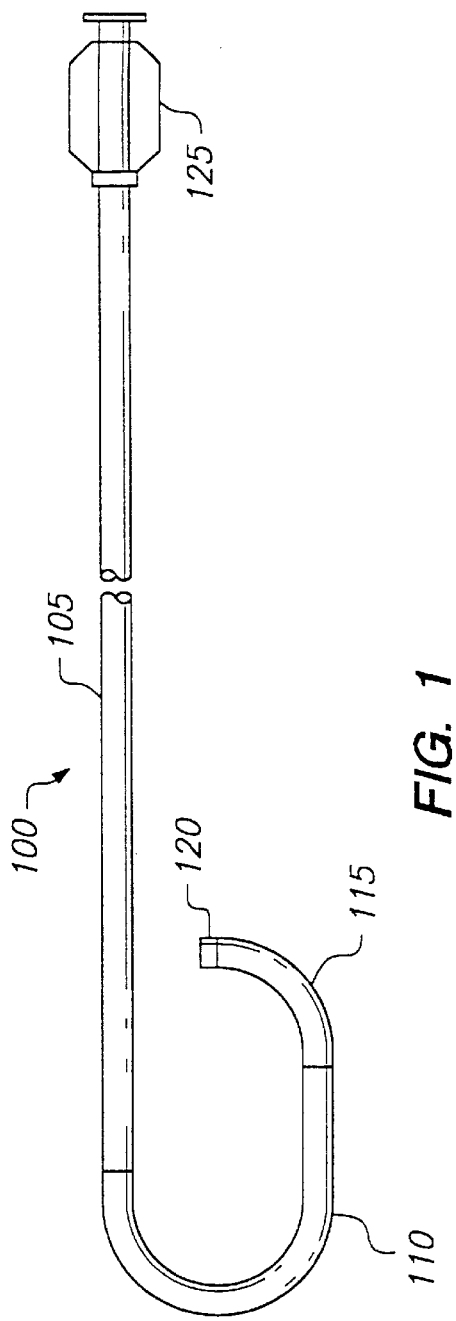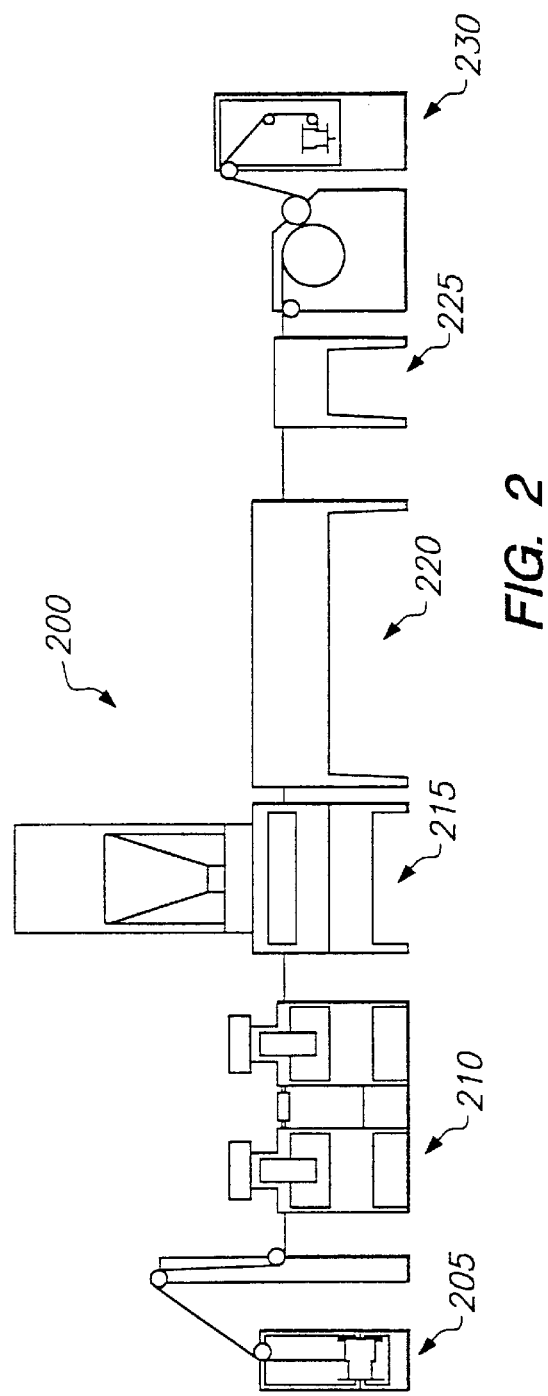

CATHETER WITH VARIABLE FLEXIBILITY PROPERTIES AND METHOD OF MANUFACTURE

This application claims the benefit of U.S. provisional application Ser. No. 60/014,552, filed Apr. 3, 1996 abandoned.

BACKGROUND OF THE INVENTION

1. Field of the Invention

This invention relates to the field of tubular medical devices and more particularly to catheters. Still more particularly, the present invention relates to intravascular catheters, such as angiographic cardiac catheters, guiding catheters, and interventional neuroradiology microcatheters.

2. Description of the Related Art

Vascular catheters and other types of catheters require remote guidance of insertion from outside of a patient. These catheters have fine spiraled or braided metallic or non-metallic strands of reinforcement material embedded in thin cylindrical walls of flexible polymer tubing. For proper operation, these types of catheters require certain performance characteristics. These catheters should transmit rotational torque accurately from a proximal end outside of a patient to a distal end inside of the patient for precise positioning. Such catheters should prevent collapse, kinking or alteration of inner lumen, and be able to contain fluid pressures up to 1,000 psi. These catheters should also be relatively stiff at the proximal end for good pushability and progressively more flexible towards the distal end to be able to maneuver through tortuous vessels without damaging the vessel wall. Furthermore, such catheters should provide the largest inside diameter at any given outside diameter (French size), i.e., to have the thinnest wall possible without compromising catheter performance. In the case of guiding catheters and microcatheters, it is desirable to have a lubricious inside surface for easy insertion of therapeutic devices, such as balloon catheters, atherectomy catheters, guidewires, and microcoils.

Reinforcement of a tubing structure is necessary when the tubing is required to withstand a variety of different mechanical stresses, such as torque, pushing, pulling, pressure, and shearing forces. A typical construction configuration of reinforced tubing, as is the case of a catheter body, is the three layer sandwich comprising a reinforcement layer encased by a base coat and top coat layer. This three layer sandwich is made by forming or extruding a first plastic layer ("base coat") into a tube over a mandrel. A braided or spirally wound metal wire or oriented plastic filament is then tightly woven over the base coat. A second plastic layer or top coat is then applied as an outer coating and is extruded, heat shrunk or dipped in a liquid polymer solution to encase the reinforcement layer. A typical catheter is shown in FIG. 1. A proximal transitional tip segment 110 and a distal transitional tip segment 115 are extruded separately and heat fused to a catheter body 105. These transitional tip segments 110, 115 are more flexible and may or may not contain a reinforcement layer. A soft, preferably radiopaque, tubular material 120 is fused to the distal transitional tip segment 115 for a less traumatic insertion into the vasculature. A Luer hub 125 is attached to the proximal end of the tubing for the connection of different accessories. In addition, the outer surface of the catheter is coated usually with a hydrophilic coating with low coefficient of friction to ease placement of the device.

Guiding catheters and microcatheters, in particular, must be able to transmit high torque for engagement and directional control and have a high inner lumen lubricity for the insertion of secondary devices such as angioplasty and atherectomy catheters, microcoils, and the like. Additionally, it is desirable that the outer diameter of the catheter be as small as possible so as to minimize trauma to the patient. The outer diameter dimension is a function of base coat and top coat width and the type of reinforcement material and braid configuration used. All of these factors must be combined in a way to achieve low kinking characteristics for the tube.

The above described manufacturing technique is very labor intensive, because the components having different physical properties are manufactured separately and assembled individually to form a catheter. A major disadvantage with that technique is that the non-reinforced tip segments are prone to break away from the reinforced body segment.

There is a need in the art for an improved design and manufacturing method for polymeric medical tubes, like intravascular catheters, to provide a method of manufacture in a more continuous fashion, reducing the number of components and required manufacturing steps.

There is also a need for providing tubular polymer profiles with variable flexibility properties along the length, as in the case of intravascular catheters, while not compromising the safety of the device.

SUMMARY OF THE INVENTION

The objective of the present invention is to provide certain tubular profiles such as catheters, for example, and a method for their manufacture.

It is another object of the present invention to provide an apparatus for the manufacture of certain tubular profiles such as catheters and the like.

It is still another object of the present invention to provide tubular profiles such as catheters as well as a method and apparatus for their manufacture wherein the catheters are manufactured from a plurality of polymeric materials having different physical properties to form a finished tubular profile having variable flexibility properties along the longitudinal extent thereof.

BRIEF DESCRIPTION OF THE DRAWINGS

FIG. 1 illustrates a typical catheter.

FIG. 2 is a schematic drawing of a commonly used electrostatic wire coating system.

DESCRIPTION OF THE INVENTION

Figure 3:
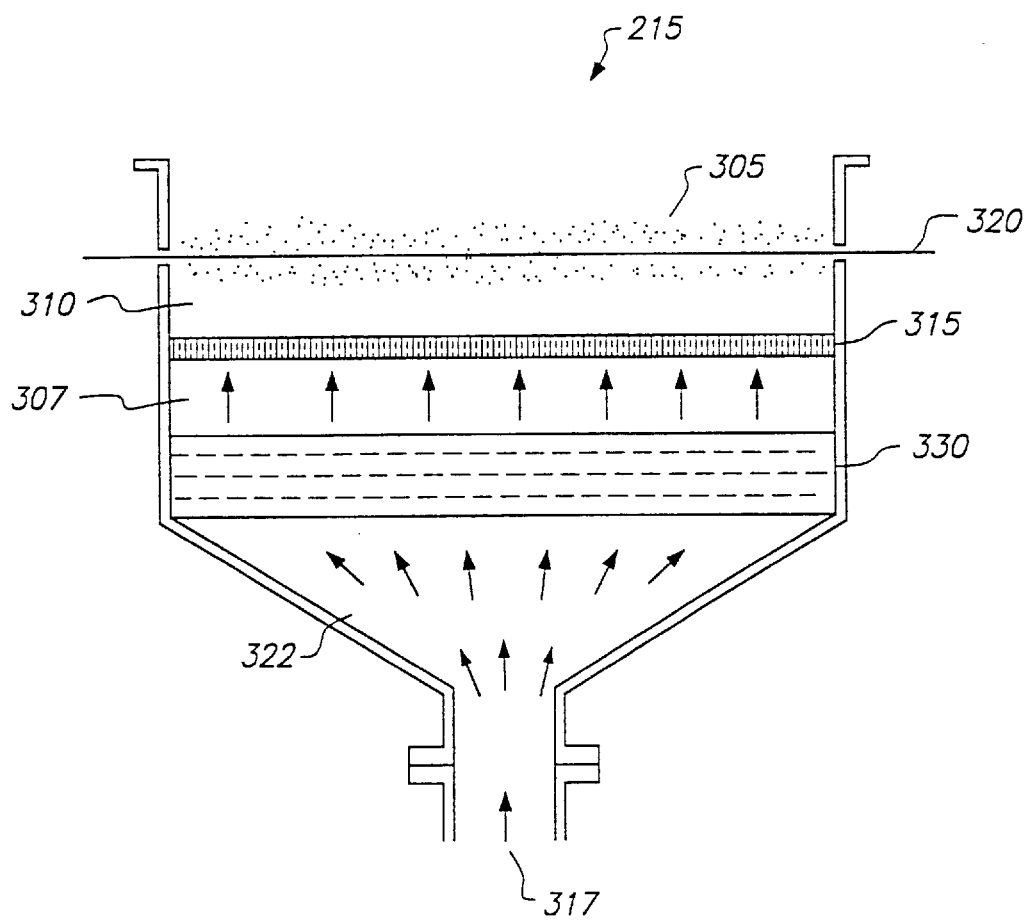
FIG. 3 is a schematical illustration of a wire coating apparatus utilizing a powder coating process.

Electrostatic powder coating is a commonly used process to create polymeric coatings on metallic surfaces for various purposes. For example, in the wire and cable industry it is being used for insulation, decorative and protective purposes. A wide variety of materials are available for powder coatings, including but not limited to: polyesters, polyimides, nylons (polyamides), polytetrafluoroethylene (PTFE), ECTFE, PFA, polyethylenes, polypropylenes, polyurethanes. The process is capable of creating pinhole free, single pass film build-up from 0.0005" to 0.020" in a controllable manner. In FIG. 2 there is shown a schematical drawing of a commonly used electrostatic wire coating system 200. In the system 200, a payout spool 205 feeds a wire through a pre-cleaning mechanism 210 in order to clean the wire before entering a wire coating apparatus 215 where powder particles are applied to the wire. A description of the powder coating process will be described below with reference to FIG. 3. After the wire is coated, it is fed through a curing oven 220 where the powder melts and becomes a homogeneous film. After leaving the oven 220, the wire is cooled by air or water in a cooling system 225, and then wrapped around a take up spool 230.

Referring now to FIG. 3, the schematical drawing illustrates a wire coating apparatus 215 utilizing a powder coating process. In a preferred embodiment, powder particles 305 are aerated in a coating chamber 310 and are electrostatically charged by ionized air 307 which passes through a porous plate 315 at the base of the chamber 310. The ionized air 307 is supplied by dry air from a dry air input 317 which is fed into an air plenum chamber 322 and then passed through a charging media 330. As the powder particles 305 become charged, they repel each other and rise above the chamber 310 forming a cloud of charged particles 305. When a grounded wire 320 is conveyed through the cloud, the charged powder particles 305, because of their opposite potential, are attracted to the wire 320. The powder particles 305 form a uniform coating, being more attracted to exposed areas than those already insulated.

The coating thickness is controlled by an applied voltage 325 to the charging media 330 and exposure time to the cloud 305. The wire 320 continues directly into the curing oven 220, where the powder melts and becomes a homogeneous film. After leaving the oven, the wire is cooled by air or water.

Figure 4:
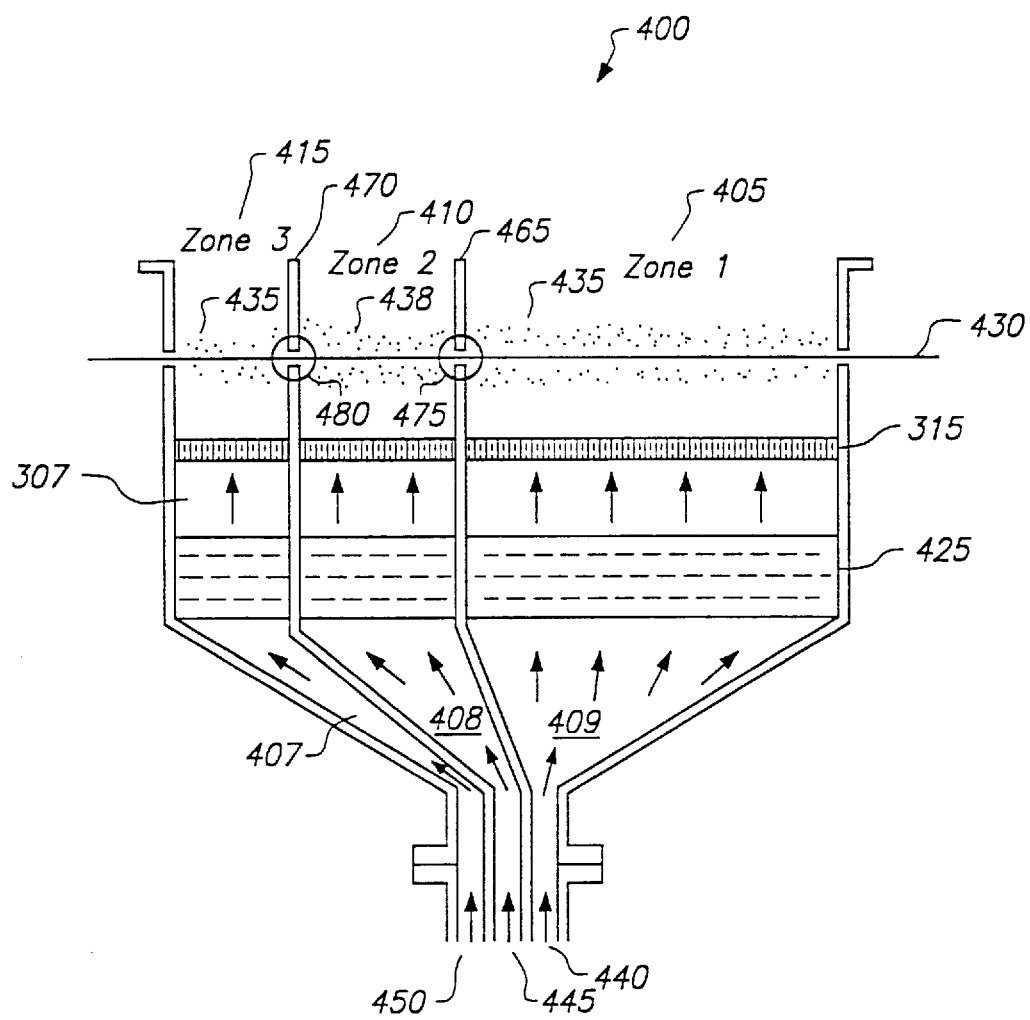
FIG. 4 is a schematical illustration of a powder coating apparatus for the manufacture of tubular profiles such as catheters according to the present invention.

Referring now to FIG. 4, a schematical drawing is shown illustrating a new improved powder coating apparatus 400 for the manufacture of tubular profiles such as catheters according to the present invention.

The apparatus includes a powder coating equipment having at least two chambers 405, 410, 415, each containing polymeric powders with different physical properties in which a tubular profile such as a catheter is formed. The method of the invention involves providing a plurality of materials deposited simultaneously to form a tubular profile such as a catheter, having variable flexibility properties along its longitudinal axis.

In accordance with the method of the present invention, a first embodiment of the variable stiffness tubing is constructed by electrostatic powder coating a mandrel wire 430 in the multi-chamber apparatus 400. This is done by simultaneously depositing polymer particles having different physical properties on the mandrel wire 430. For example, the width of the first chamber 405 (Zone 1) could be 90 cm, and would contain polymer particles having a flexural modulus between 160 and 200 kpsi, while the width of the second chamber 410 (Zone 2) could be 7 cm, and contain polymer powders with a flexural modulus of 60 to 100 kpsi and the width of the third chamber 415 (Zone 3) could be 3 cm, and contain polymer powders with a flexural modulus of 15 to 30 kpsi. The wall thickness of the polymeric tube is controlled by the applied voltage 420 to the charging media 425 and exposure time of the mandrel wire 430 to the polymeric particle cloud 435. Each chamber 405, 410, 415 has its own dry air supply 440, 445, 450 feeding into its own air plenum chambers 407, 408, 409, respectively. Each chamber 405, 410, 415 also has its own high voltage DC power supply 420, 455, 460 to control the wall thickness of each segment individually. The width of each chamber 405, 410, 415 is adjustable by moving the dividing walls 465, 470 in the apparatus 400. The dividing walls 465, 470 contain apertures 475, 480 through which the mandrel wire 430 is conveyed.

Figure 5:
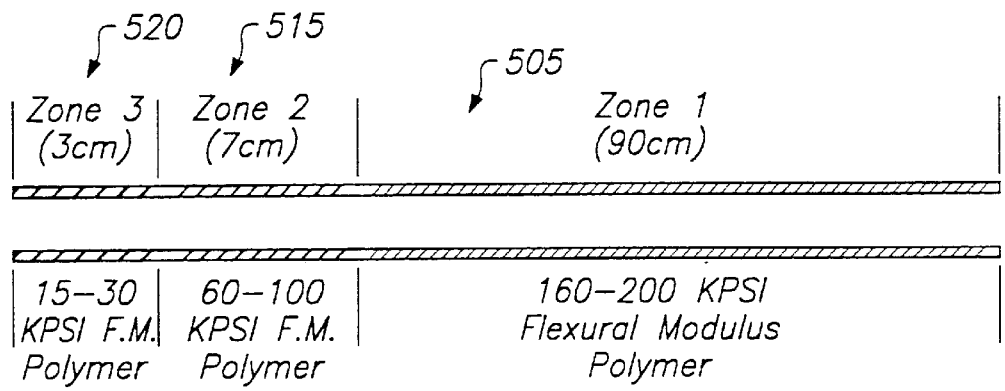
FIG. 5 illustrates the flexural moduli of various segments of a catheter manufactured according to one embodiment of the method of the present invention.

After deposition of the powder particles, the mandrel wire 430 moves into the curing oven 220, where the powder melts and becomes a tubular polymeric film. After leaving the oven 220, the polymer layer is cooled by air or water and cut to length. By removing the mandrel wire, a polymeric tube such as a catheter is provided with variable flexibility properties. FIG. 5 illustrates the flexural moduli of various segments 505, 515, 520 of a catheter manufactured according to the method of the present invention.

A plurality of segments can be provided with different flexibility properties by adding deposition chambers to the apparatus 400. A particular advantage of the process is that the length of these segments 505, 515, 520 can be controlled very precisely by controlling the width of the deposition chambers 405, 410, 415. An additional advantage is that short transitional segments, in the range of 0.062" to 0.250" in length, are created where the powder particles mix between two consecutive chambers, providing a less abrupt transition, which improves the kink resistance of the tube. The lengths of these short transitional segments can be controlled by varying the size of the apertures 475, 480 in the dividing walls 465, 470. Thus, the catheter or other tubular profile is manufactured with varying properties along its longitudinal axis corresponding to the properties of the constituent powdered polymeric materials which are deposited by the coating chambers 405, 410, 415. By using polymeric materials with different colors, identification of the variable flexibility segments is easily accomplished.

In an alternate embodiment, wherein the tube comprises an inner and outer hydrophilic layer, while the structural middle layer provides the variable flexibility properties, the method steps include first depositing polymer particles having hydrophilic properties on the mandrel wire 430 by an electrostatic coating process. The thickness of this layer for example could be between 0.0005" to 0.001". In a preferred embodiment, the electrostatic coating process as described with reference to FIG. 3 is used, however, one skilled in the art will recognize that other types of electrostatic coating processes could be used.

Figure 6:
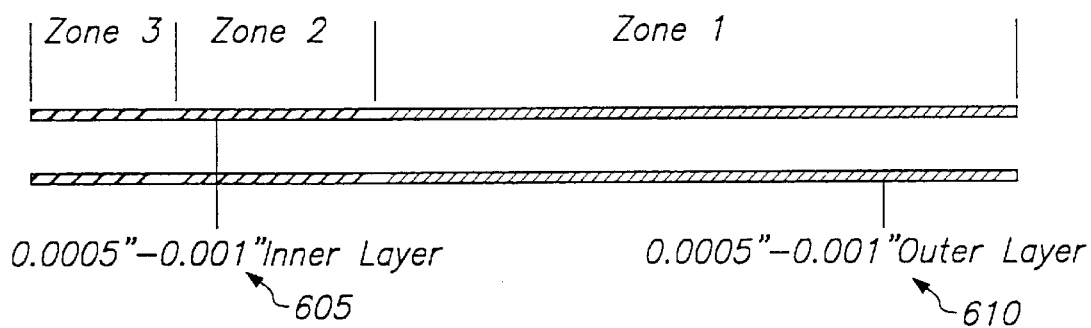
FIG. 6 illustrates the locations and thicknesses of inner and outer hydrophilic layers of a catheter manufactured according to one embodiment of the method of the present invention.

Next, the mandrel wire 430 with the first layer of polymer particles enters the above described multi-chamber coating apparatus 400, wherein polymer powders with different physical properties are simultaneously deposited. Then the mandrel wire 430 moves into another coating apparatus and again a hydrophilic type polymer powder is deposited on the order of 0.0005" to 0.001" thickness. FIG. 6 illustrates the locations and thicknesses of the inner hydrophilic layer 605 and the outer hydrophilic layer 610 a catheter manufactured according to the method of the present invention.

After deposition of all powder particles, the mandrel wire 430 moves into the curing oven, where the powder melts and becomes a composite polymeric film. After leaving the oven, the composite polymer layer is cooled by air or water and cut to length. By removing the mandrel wire 430, a composite polymeric tube is provided with an inside and outside hydrophilic surface in addition to having the variable flexibility properties.

In an alternate embodiment wherein the tube comprises a reinforcement layer, the method steps include first forming a base coat layer over the mandrel wire in a powder coating apparatus and curing oven. For tubing applications where inner lumen lubricity is of the utmost importance, such as in guiding catheters or microcatheters, it is preferred to use fluoropolymers as the base coat material. In other applications, the base coat is constructed from the same polymer material as the top coat. After formation of the base coat layer, a wire reinforcement is formed through a known spiral weaving process into a braided annular configuration which is tightly overlaid onto the base coat. A plastic top coat layer is then added by the above described multichamber powder coating apparatus 400 to complete the composite tube construction with varying flexibility properties. In the case of using a fluoropolymer such as PTFE or FEP as a base coat material, the outside surface of the polymer is chemically etched with a known TETRA-ETCH™ solution or plasma—treated for better adhesion either before or after the formation of the reinforcement layer.

Figure 7:
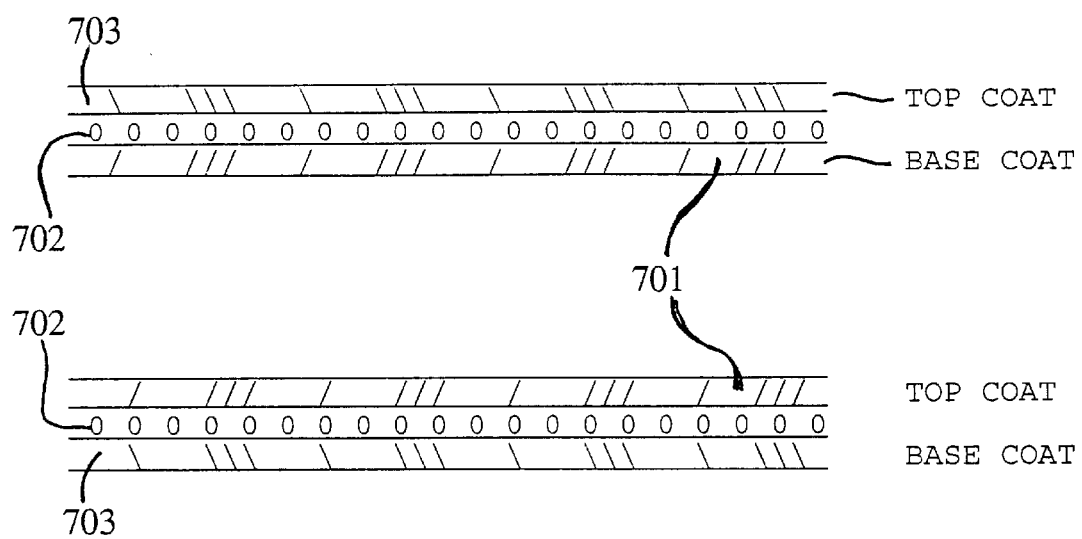
FIG. 7 is a cross-sectional view of an embodiment including a wire reinforcement layer between the base coat and top coat.

In accordance with another embodiment, the individual strands or filaments of the wire braid material are coated with a plastic material of the type compatible with the typical polymeric materials used for the inner and outer layers (base and top coat) of conventional three-layer reinforced tubing members. FIG. 7 shows a cross-section of this embodiment, in which the wire braid material 702 is formed on base coat 701, with top coat 703 being formed on the wire braid 702. Coating materials used for commercially available coated wire comprises a variety of polymers, including, but not limited to polyurethane, polyester, polyamide, polyimide and PTFE. A known "liquid coating" technology is used to deposit these materials on the wire in extremely thin layers on the order of 0.0002".

First, the individual coated wires are formed directly over the mandrel into a spiral or braided reinforcement configuration. Before entering the powder coating apparatus, the wires are pre-heated to increase adhesion between the reinforcement and top coat layer materials. This improved adhesion characteristic creates a unique opportunity to construct a more cohesive tubular structure.

In view of the improved adhesion offered by the individual coated wire strands, the conventional three-layer composite reinforced catheter structure, typically comprising a reinforcement layer sandwiched between a base coat layer and a top coat layer, can now be modified to an improved thinner and more cohesive two-layer construction comprising only a top coat layer and a coated wire reinforcement layer. By eliminating the need for a base coat layer, an enlarged inside diameter catheter structure can be created. Also, by providing a lubricious inner coating, a large inner diameter guiding catheter can be constructed.

The enlarged inside diameter permits a larger flow rate, or in the case of a guiding catheter, a larger diameter inner lumen permits the insertion of larger medical devices such as angioplasty balloon catheters, stents, and atherectomy devices.

Selective deposition and removal technique

In a different embodiment, multiple numbers of coating chambers could be lined up consecutively, containing the polymeric powders with different physical properties. The mandrel wire would then pass through the first chamber and powder particles would deposit to the entire surface, but before entering the oven for melting, on certain places circumferentially the powder particles would be removed selectively by blowing and/or vacuuming them away. The wire then would enter the second chamber, where powder particles having substantially different flexural modulus would be deposited only to those selectively cleaned areas, and this process could be repeated again and again, depending on how many segments with different flexural properties are required.

While a preferred embodiment of the present invention has been described in detail herein, it will be appreciated that changes and modifications can be made by those skilled in the art to the described embodiment without department from the true spirit and scope of the invention.

I claim:

1. A catheter with varying flexibility properties along its longitudinal axis comprising:

a first tubular segment formed from a first polymeric material having a first flexibility property;

a second tubular segment, adjacent the first tubular segment, formed from a combination of the first polymeric material and a second polymeric material having a second flexibility property; and a third tubular segment, adjacent the second tubular segment, formed from the second polymeric material, the second tubular segment forming a seamless transition between the first tubular segment and the third tubular segment.

2. The catheter of claim 1, further comprising an inner tubular layer disposed longitudinally within the first, second, and third tubular segments, the inner tubular layer comprising polymer particles having hydrophilic properties.

3. The catheter of claim 2, further comprising an outer tubular layer overlying the first, second, and third tubular segments, the outer tubular layer comprising polymer particles having hydrophilic properties.

4. The catheter of claim 1, further comprising a braided reinforcement tubular layer disposed longitudinally within the first, second, and third tubular segments, the braided reinforcement tubular layer made of wires individually-coated with polymeric materials.

5. The catheter of claim 1, further comprising an inner tube disposed longitudinally within the first, second, and third tubular segments.

6. The catheter of claim 5 wherein the inner tube is comprised of a fluoropolymer material.

7. The catheter of claim 5, further comprising wire-braid material disposed intermediate the inner tube and the first, second, and third tabular segments.

8. The catheter of claim 7, where in the wire-braid material is polymer-coated.

9. A method of manufacturing a catheter having a plurality of tubular segments along its longitudinal axis, each tubular segment having a different flexibility property, the method comprising:

presenting a grounded wire in a plurality of adjacent coating chambers separated by movable walls, each one of the plurality of chambers containing an aerated powder of charged polymer particles having a flexibility property, each of the chambers having clearance holes through which the grounded wire extends into adjacent chambers;

depositing the charged polymer particles of the plurality of chambers on the grounded wire, charged polymer particles from adjacent chambers mixing in the hole between the adjacent chambers to provide a short transitional region of mixed polymer particles deposited on the portion of the wire extending through the hole;

removing the wire with the deposited polymer particles from the plurality of chambers;

applying heat to the deposited polymer particles;

cooling the deposited polymer particles to form a polymeric film; and removing the wire from the film to form a polymeric tube having a short seamless transition region composed of mixed polymer material.

10. The method of claim 9, further comprising selecting the lengths of the tabular segments by adjusting the walls of the coating chambers.

11. The method of claim 10, wherein selecting the lengths of the tubular segments further comprises adjusting sizes of apertures in the walls of the coating chambers.

12. The method of claim 9, further comprising:

depositing polymer particles having hydrophilic properties on the grounded wire before presenting the grounded wire in the plurality of adjacent coating chambers; and depositing polymer particles having hydrophilic properties on the grounded wire after depositing the charged polymer particles of the plurality of chambers on the grounded wire.

13. The method of claim 9, further comprising:

before presenting the grounded wire in the plurality of adjacent coating chambers, forming a base coat layer of a polymer material over the grounded wire; and overlaying a braided annular configuration onto the base coat.

14. The method of claim 13, wherein the polymer material of the base coat is a fluoropolymer material.

15. The method of claim 13, wherein the base coat layer is comprised of deposited and heat-cured polymer particles.

16. The method of claim 9, further comprising:

forming a braided reinforcement tubular layer over the grounded wire before presenting the grounded wire in the plurality of adjacent coating chambers, the braided reinforcement layer made of wires individually-coated with polymeric materials.

17. A method of manufacturing a catheter having a plurality of tubular segments along its longitudinal axis, each segment having a different flexibility property, the method comprising:

presenting a grounded wire in a first coating chamber containing a first set of charged polymer particles having a first flexibility property;

depositing the first set of charged polymer particles on the grounded wire;

selectively removing a portion of the first set of deposited charged polymer particles from at least one portion of the wire;

presenting the grounded wire in a second coating chamber containing a second set of charged polymer particles having a second flexibility property different from the first flexibility property;

depositing the second set of charged polymer particles on at least one of the portions of the grounded wire from which a portion of the first set of deposited charged particles was removed;

removing the wire with the deposited polymer particles from the second coating chamber;

applying heat to the deposited polymer particles;

cooling the deposited polymer particles to form a polymeric film; and removing the wire from the film to form a polymeric tube.

18. A method of manufacturing a catheter comprising:

presenting a grounded wire in a coating chamber containing an aerated powder of charged polymer particles having a flexibility property;

depositing the charged polymer particles on the grounded wire;

removing the wire with the deposited polymer particles from the chamber;

applying heat to the deposited polymer particles;

cooling the deposited polymer particles to form a polymeric tube; and removing the wire from the polymeric tube.

19. The method of claim 18, wherein the charged polymer particles are made of a fluoropolymer material.

20. An apparatus for manufacturing a catheter with varying flexibility properties along its longitudinal axis, the apparatus comprising:

a first coating chamber configured to contain a first set of charged polymer particles having physical properties;

a second coating chamber adjacent to the first coating chamber and separated from the first coating chamber by a movable wall, the second coating chamber configured to contain a second set of charged polymer particles having different physical properties than the first set of charged polymer particles of the first coating chamber, the movable wall having a hole extending between the first and second coating chambers;

a first dry air supply device coupled to the first coating chamber to send air to the first chamber for aerating the first set of charged polymer particles;

a second dry air supply device coupled to the second coating chamber to send air to the second chamber for aerating the second, set of charged polymer particles;

a first charging media and a first voltage power supply coupled thereto disposed for charging the first set of polymer particles in the first coating chamber; and a second charging media and a second voltage power supply coupled thereto disposed for charging the second set of polymer particles in the second coating chamber, a wire extending through the first coating chamber, through the hole, and through the second coating chamber, charged polymer particles of the first and second sets mixing in the vicinity of the hole to form a short, seamless transition between sections of the catheter formed on the wire in the first and second coating chambers.

21. The catheter of claim 1 wherein the second tubular segment has a length along its longitudinal axis which is very much shorter than the lengths of the first and third tubular segments.

* * * * *